United States Patent [19]

Judet

[11] Patent Number: 5,429,639
[45] Date of Patent: Jul. 4, 1995

[54] SPINE FIXATOR FOR HOLDING A VERTEBRAL COLUMN

[75] Inventor: Thierry Judet, Ville D'Avray, France

[73] Assignee: Tornier S.A., Saint-Ismier, France

[21] Appl. No.: 239,896

[22] Filed: May 9, 1994

[30] Foreign Application Priority Data

May 17, 1993 [FR] France .................. 93 06175

[51] Int. Cl.⁶ .................. A61B 17/70; A61B 17/80
[52] U.S. Cl. .................. 606/61; 606/69; 403/362
[58] Field of Search .......... 606/61, 60, 69, 70, 606/71; 403/362, 347

[56] References Cited

U.S. PATENT DOCUMENTS

| 3,125,397 | 3/1984 | McGrath | 403/362 |
| 3,638,173 | 1/1972 | Middendorf et al. | 403/362 |
| 4,946,458 | 8/1990 | Harms et al. | 606/61 |
| 5,002,542 | 3/1991 | Frigg | 606/61 |
| 5,129,899 | 7/1993 | Small et al. | 606/73 |
| 5,190,543 | 3/1993 | Schläpfer | 606/61 |
| 5,209,751 | 5/1993 | Farris et al. | 606/61 |

Primary Examiner—Stephen C. Pellegrino
Assistant Examiner—Scott B. Markow
Attorney, Agent, or Firm—Dowell & Dowell

[57] ABSTRACT

A spinal fixator comprising two substantially parallel assemblies each which includes a slideway having an open slot therein, a plurality of rings which define a slideway opening having a profile corresponding to that of the slideway, each ring having a bore aligned with a hole in the bottom of the ring through which pedicular screws having a head and self-tapping threads are disposed, and caps secured in the bore of each ring.

19 Claims, 4 Drawing Sheets

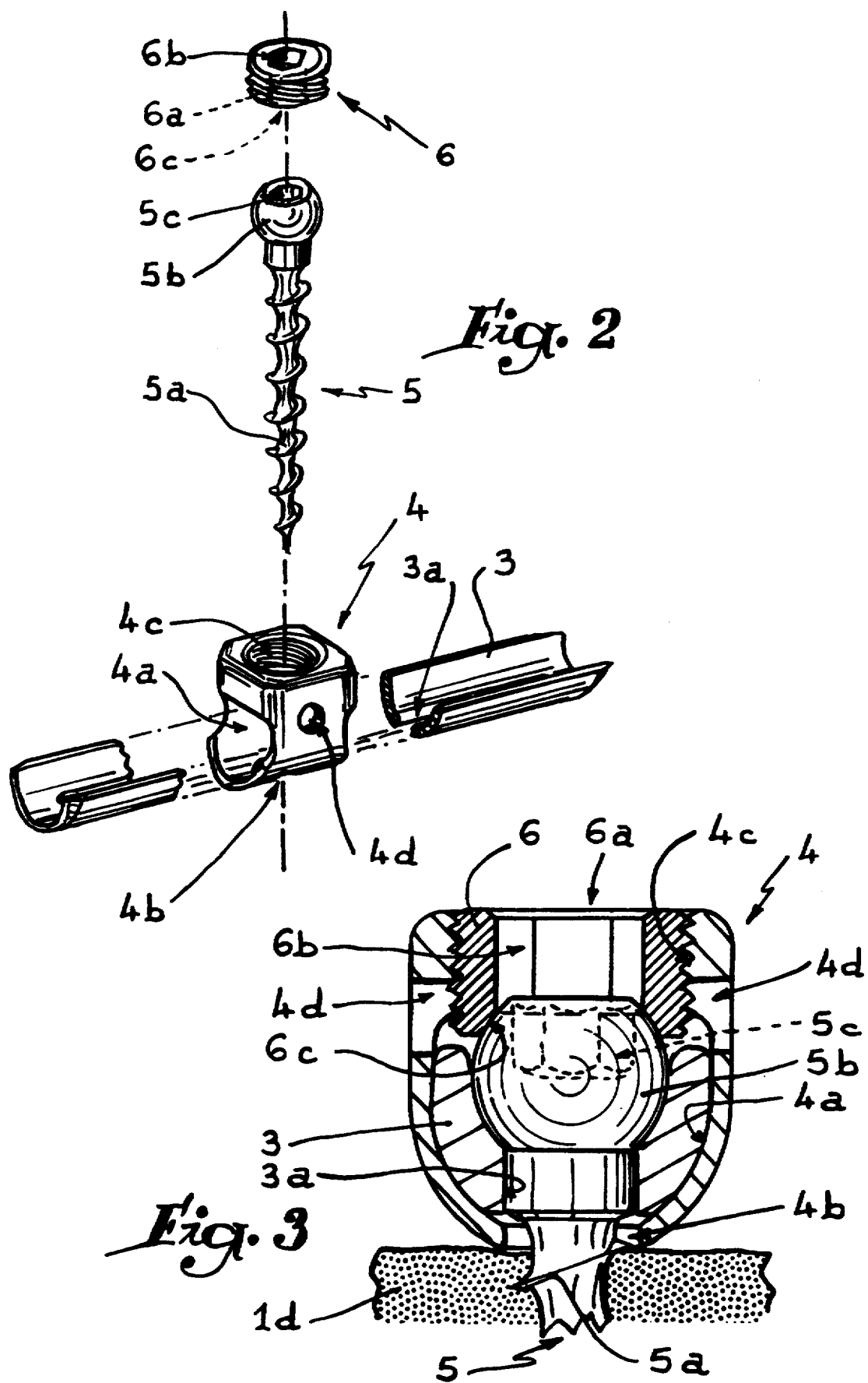

SPINE FIXATOR FOR HOLDING A VERTEBRAL COLUMN

BACKGROUND OF THE INVENTION

1. Field of the Invention

The present invention relates to a spine fixator for aligning and holding a backbone.

2. History of the Related Art

Fixators of this type are known, which generally comprise two parallel assemblies, each comprising:

a cylindrical rod whose length is determined as a function of the number of stages to be joined;

and a plurality of assemblies composed of a ring, a nut and a pedicular screw or of hooks allowing the rods to be fixed on the vertebrae.

Other fixators comprise plates perforated with holes or slots allowing passage of screws being implanted in the pedicles.

Such fixators present certain drawbacks concerning the risks of micro-movements or of fragility of the connection either between the screw and the rod or between the screws and the plates.

Moreover, the fixators employing plates impose a pedicular spacing which may not be adapted to anatomic variations.

It is a particular object of the present invention to overcome these drawbacks.

SUMMARY OF THE INVENTION

To that end, the spine fixator according to the present invention comprises two substantially parallel assemblies which are each constituted by:

a slideway in the form of a U having a bottom is pierced with an open slot therein;

a plurality of rings which have a horizontal opening if an inner profile corresponding to that of the slideway, a tapped bore coaxial with a smooth hole in the bottom of the ring perpendicularly to the opening;

pedicular screws with self-tapping thread and spherical head, allowing the slideway to be put in place and positioned in the ring;

and a threaded cap screwed in the tapped bore of each ring and which each abut on the upper part of the head of the screw so as to assemble by tightening the ring and the slideway via the head of the screw.

BRIEF DESCRIPTION OF THE DRAWINGS

The invention will be more readily understood on reading the following description with reference to the accompanying drawings, in which:

FIG. 2 is a perspective assembly view showing, in detail, the different elements composing each assembly of the spine fixator.

FIG. 3 is a section along III—III (FIG. 1) representing the immobilization of one of the assemblies of the fixator.

DESCRIPTION OF PREFERRED EMBODIMENT

Figure 1:
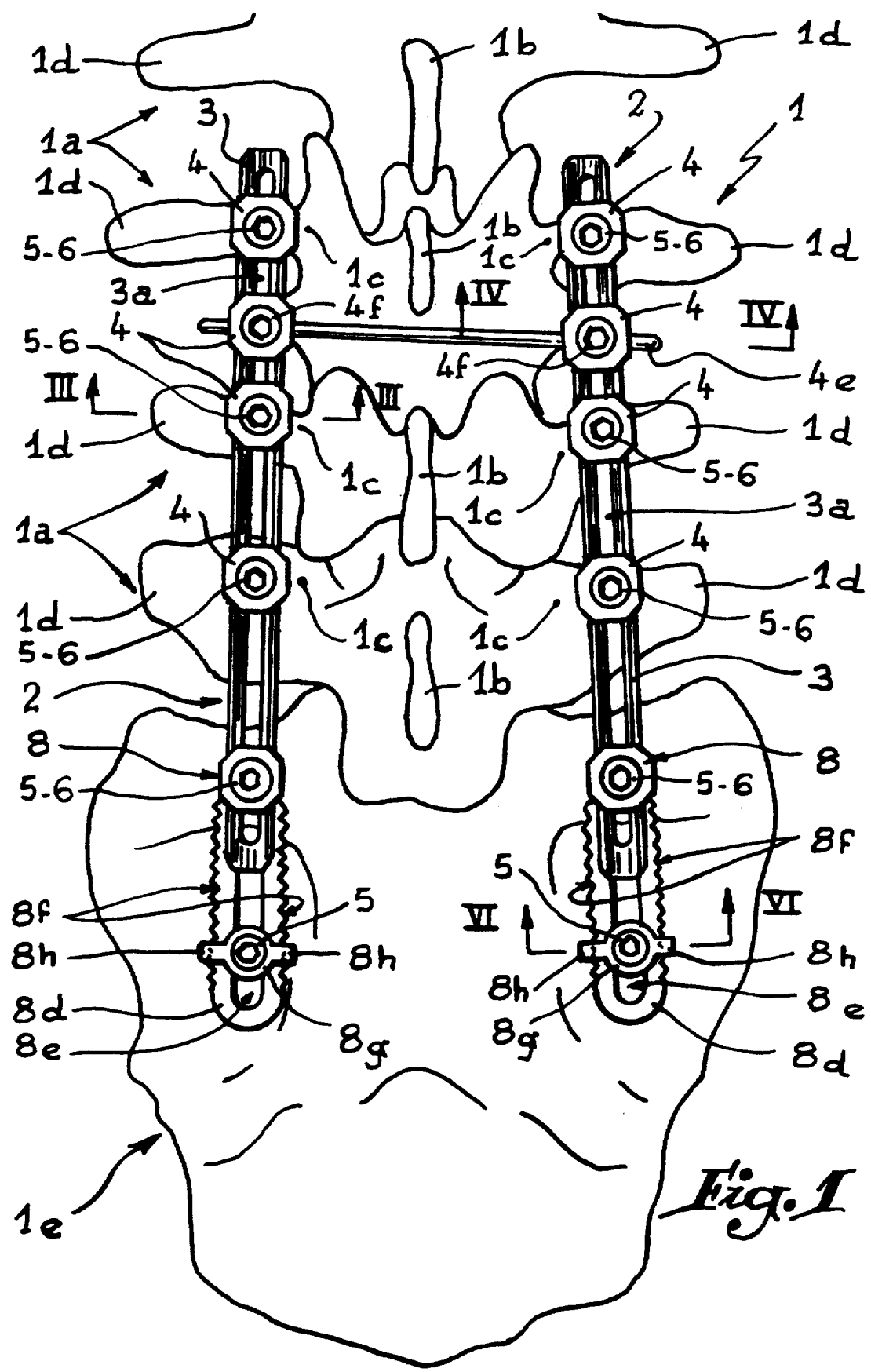
FIG. 1 is a view in elevation illustrating the different elements composing the spine fixator according to the invention.

Referring now to the drawings, FIG. 1 shows part of a spinal column 1 comprising vertebrae 1a which are joined to one another by a fixator 2, in order to effect a fusion of the vertebral stages. The fixator 2 comprises two substantially parallel assemblies which are placed on either side of the spinous apophyses 1b and immobilized on the pedicles 1c of the transverse apophyses 1d.

FIGS. 2 and 3 show the different elements which compose each fixator 2 and in particular two slideways 3 which are generally curved either in convex manner or in concave manner depending on the morphology of the rachidian segment to be fixed and the correction to be obtained. The length of each slideway is chosen to be adapted to the number of vertebrae 1a to be joined. Each slideway 3 has a profile in the form of a U having a bottom with, over a large part of its length with, a slot 3a.

A ring 4 having an outer profile which is square in its upper part and rounded in its lower part, has along its horizontal axis with an opening 4a. This latter presents the same U-shaped inner profile as the outer profile of the slideway 3. In the bottom of the ring 4 is a vertical hole 4b which opens to the outside from the opening 4a. In the upper part of the ring 4 and opposite the hole 4b and along the same vertical axis, there is provided a tapped bore 4c which communicates with the opening 4a.

Moreover, the ring 4 comprises a hole 4d which is provided in the same horizontal plane as the opening 4a, but perpendicularly thereto. Hole 4d lies between the bore 4c and the opening 4a.

A screw 5 allows assembly of the constituent elements of the fixator on each vertebra 1a of the spinal column 1. It comprises a self-tapping thread 5a and a spherical head 5b which has at its center and in its upper part, a hexagonal hole 5c.

Finally, a threaded cap 6 is provided to cooperate with the tapped bore 4c of ring 4. This cap has a vertical hole 6a which presents in its upper part a hexagon socket profile 6b, while its lower part forms a portion of sphere 6c having the same diameter as the spherical head 5b of the screw 5.

Figure 4:
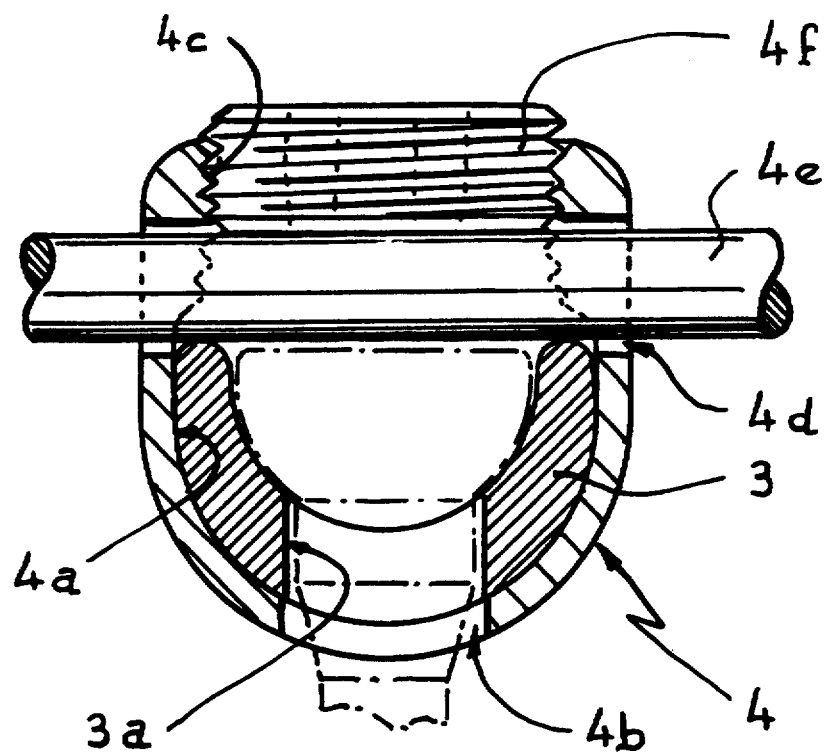
FIG. 4 is a section along IV—IV (FIG. 1) showing the transverse stabilization device.

FIG. 4 shows the ring 4 which is used as complementary ring for joining together the assemblies of the fixator 2 for transverse stabilization thereof.

Figure 5:
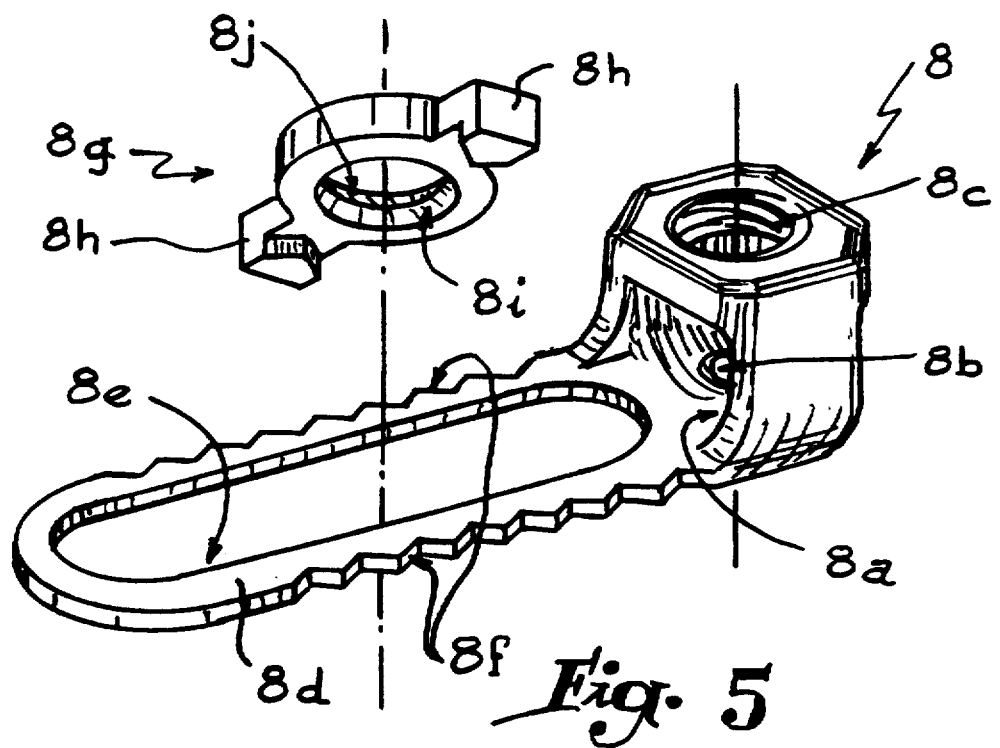
FIG. 5 is a view in perspective illustrating another particular ring of the spine fixator which is intended to fix two assemblies on the sacrum.

Hole 4d is designed to receive one of the ends of a rod 4e which is tightened by means of threaded cap 4f on the slideway 3. The other end of rod 4e is immobilized in the same manner in another ring 4 which is provided on the other assembly, as shown in FIGS. 1 and 5. Rings 4 are generally provided between two other rings of an assembly so that rod 4e may pass freely between two spinous apophyses 1b.

A screw may possibly be interposed in the transverse fixation device in order to improve positioning of the fixator as is shown in dashed and dotted lines in FIG. 4.

The connection between the assemblies by means of the rod 4e makes it possible to rigidify the spine fixator 2.

Figure 6:
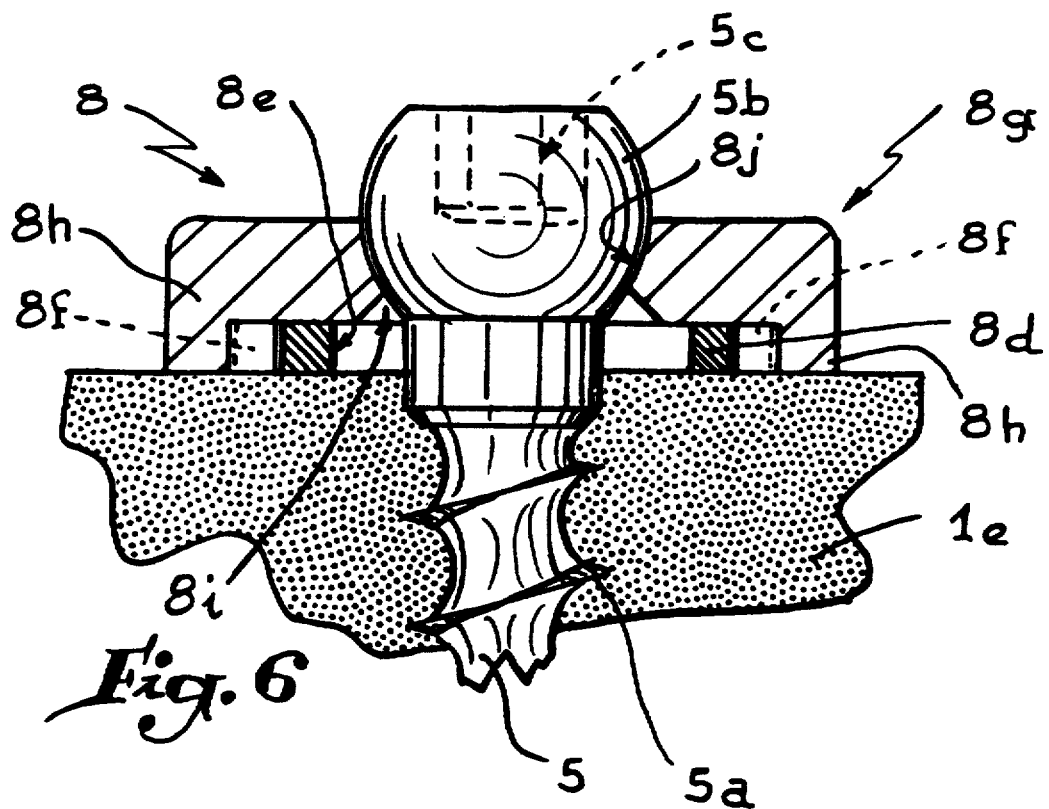
FIG. 6 is a section along VI—VI (FIG. 1) showing the fixation of the ring shown in FIG. 5 in the sacrum.

FIGS. 5 and 6 show a ring 8 which is designed in the same manner as ring 4. Ring 8 comprises a horizontal U-shaped opening 8a, a hole 8b which is provided in the bottom of the ring and a tapped bore 8c which is disposed opposite hole 8b. The tapped bore 8c receives a threaded cap identical to the one described and referenced 6.

The bottom of ring 8 is secured, in line with the bottom of the horizontal opening 8a, with an elongated plate 8d. Plate 8d has an oblong slot 8e and possibly includes teeth 8f on each of its outer edges.

Finally, a washer 8g is provided, which comprises on its periphery two opposite projections 8h provided with inner teeth which cooperate upon assembly with those of the plate 8d. Washer 8g has a central hole 8i which comprises an outer bevel 8j of concave profile presenting the same radius as that of the spherical head 5b of the screw 5.

The ring 8 is used in those cases where a hold in the sacrum is necessary in order to complete the fixation provided on the last vertebra 1a, being given that the lumbar-sacral hinge is the seat of the greatest efforts.

In fact, ring 8 is fixed on the first vertebra of the sacrum 1e in the same manner as ring 4 as described previously, while plate 8d is immobilized on the second vertebra of the sacrum 1e via the washer 8g and a pedicular screw 5b.

The operator must proceed as follows to position the fixator 2 described hereinabove on the vertebral column 1.

The operator prepares the first assembly constituting the fixator 2 as a function of the number of vertebrae 1a to be immobilized, i.e. The operator introduces on the slideway a certain number of rings 4. Certain rings 4 are placed between two other rings 4 as a function of the number of transverse connections that the operator desires to make between the two assemblies.

The operator introduces inside each ring 4 a screw 5 which cooperates with the slot 3a of the slideway 3 and the hole 4b.

The operator tightens the screws 5 inside the pedicles 1c of each vertebra 1a.

The operator screws the threaded caps 6 in the tapped bores 4c of the rings 4 so that they abut on the upper part of the head 5b of the screws 5. Simultaneously, by tightening the caps 6, the slideway 3 and the rings 4 may block against the lower part of the cylindrical head 5b of the screws 5 (FIG. 3).

The operator proceeds in the same manner for positioning the second assembly of the fixator 2.

The operator then screws the threaded caps 4f of the complementary rings 4 of the two assemblies to immobilize the rods 4e previously introduced in the holes 4d in order to rigidify the fixator 2 (FIGS. 1 and 3).

When, for reasons of pathology, the operator must assemble the fixator on the sacrum 1e, he uses a ring 8 described previously is used.

It is ascertained that the particular structure of the rings 8 makes it possible to reduce the dimensions in height at the place where the vertebral column is covered only by a fine thickness of skin.

It will be noted that the different rings 4 and 8 hug the pedicular screws 5 and the slideway 3 tightly, giving a rigidity to the assembly since they limit the deformation of the slideway 3 during tightening of the screws 5.

The solidity of the joint between screws and slideway is ensured directly by the tightening of the caps on the head of the screws and indirectly by the elastic deformation of the rings laterally tightening the slideway on the spherical base of the screws.

It will be noted that the assemblies composing the spine fixator may be used solely for joining vertebrae 1a together without u,sing the ring 8.

The spine fixator according to the invention makes it possible to obtain a relative suppleness between the instrumented vertebrae as well as a very stable fixation in the vertebrae.

It must, moreover, be understood that the foregoing description has been given solely by way of example and that it in no way limits the domain of the invention which would not be exceeded by replacing the details of execution described by any other equivalents.

What is claimed is:

1. A spinal fixator for aligning and holding a vertebral column, comprising two spaced assemblies, each of the assemblies including:
   a. a slideway having a U-shaped cross section with a bottom portion, an open slot in said bottom portion;
   b. a plurality of first rings, each of said first rings having upper and lower portions and opposing side walls, each of said first rings defining a slideway opening of a profile to cooperatively receive said slideway therethrough, each of said first rings including a bore in said upper portion which is aligned with a hole in said lower portion thereof and which hole is oriented generally perpendicularly to said slideway opening;
   c. a plurality of pedicular screws each having a self-tapping thread portion and a head portion, said self-tapping thread portion being of a size to extend through said hole in said lower portion of said first rings and said head portion being of a size to be receivable within said first rings through said bore in said upper portion thereof; and
   d. a plurality of cap means receivable within said bores of said first rings, whereby after said slideway is received through said slideway openings in a plurality of spaced first rings, pedicular screws are inserted with their self-tapping thread portions extending through said holes in said bottom portions of said first rings so that said head portions are seated within said slideway and said cap means are received in said bores to thereby secure said slideway relative to said first rings.

2. The spinal fixator of claim 1 wherein each first ring is provided with a side opening in at least one of said side walls thereof.

3. The spinal fixator of claim 2 wherein said assemblies are connected by at least one rod extending therebetween, said rod having first and second ends, said first end being received within said side opening of one of said first rings of one of said assemblies and said second end of said rod being received within said side opening of one of said first rings of the other of said assemblies.

4. The spinal fixator of claim 3 in which each of said assemblies includes a second ring having upper and lower portions and opposing side walls, each of said second rings defining a slideway opening of a profile to cooperatively receive said slideway therethrough, said second rings having a bore in said upper portion thereof which is aligned with a hole in said lower portion thereof, cap means receivable within said bore of said second ring, and said second ring including a plate extending outwardly from said lower portion thereof.

5. The spinal fixator of claim 4 in which said first rings have side openings in each of said side walls, and said rod being received through said side openings in said side walls of said one of said first rings of each of said assemblies.

6. The spinal fixator of claim 4 in which said plate includes a pair of opposite outer edges, a slot defined between said outer edges and through said plate, a plurality of spaced teeth extending outwardly in opposite directions along each of said outer edges, a washer means selectively engagable with said plate in overlaying relationship with respect to said slot therein, said washer means having a pair of projections extending on opposite sides thereof, each of said projections including a tooth which is cooperatively receivable between said teeth of said plate.

7. The spinal fixator of claim 6 in which said washer means includes an opening, at least one of said pedicular screws being mounted with said self-tapping thread portion extending through said opening in said washer means and through said slot in said plate with said head portion thereof seated against said washer means.

8. The spinal fixator of claim 7 wherein said opening in said washer means is defined by a concave bevelled edge, and said head of said at least of said one pedicular screws has a profile which is complementary to the concave bevelled edge of said opening in said washer.

9. The spinal fixator of claim 8 wherein each of said first and second rings includes an outer profile in which said upper portions are relatively square and said lower portions are generally rounded.

10. The spinal fixator of claim 1 in which each of said assemblies includes a second ring having upper and lower portions and opposing side walls, each of said second rings defining a slideway opening of a profile to cooperatively receive said slideway therethrough, said second rings having a bore in said upper portion thereof which is aligned with a hole in said lower portion thereof, cap means receivable within said bore of said second ring, and said second ring including a plate extending outwardly from said lower portion thereof.

11. The spinal fixator of claim 10 in which said first rings for each of said assemblies include a side opening in one of the side walls thereof, and a rod extending between at least one of said first rings of each of said assemblies and having opposite ends extending into said side openings in said side walls of said at least one of said first rings of each of said assemblies, said opposite ends of said rod being engagable by said cap means to thereby secure said rod to said at least one of said first rings of each of said assemblies.

12. The spinal fixator of claim 11 wherein each of said at least one of said first rings further includes an additional opening in the other side wall, said additional opening being aligned with said side opening.

13. The spinal fixator of claim 11 in which said head portion of said pedicular screws is generally spherical and each of said cap means includes a lower surface having an arcuate profile which is complementary to said head portion of said pedicular screws.

14. The spinal fixator of claim 13 in which said plate includes a pair of opposite outer edges, a slot defined between said outer edges and through said plate, a plurality of spaced teeth extending outwardly in opposite directions along each of said outer edges, a washer means selectively engagable with said plate in overlaying relationship with respect to said slot therein, said washer means having a pair of projections extending on opposite sides thereof, each of said projections including a tooth which is cooperatively receivable between said teeth of said plate.

15. The spinal fixator of claim 14 in which said washer means includes an opening, at least one of said pedicular screws being mounted with said self-tapping thread portion extending through said opening in said washer means and through said slot in said plate with said head portion thereof seated against said washer means.

16. The spinal fixator of claim 1 in which said head portion of said pedicular screws is generally spherical and each of said cap means includes a lower surface having an arcuate profile which is complementary to said head portion of said pedicular screws.

17. A spinal fixator for aligning and holding a vertebral column, comprising two spaced assemblies, each of the assemblies including:
 a. a slideway having a U-shaped cross section with a bottom portion, an open slot in said bottom portion;
 b. a plurality of first rings, each of said first rings having upper and lower portions and opposing side walls, each of said first rings defining a slideway opening of a profile to cooperatively receive said slideway therethrough, each of said first rings including a bore in said upper portion which is aligned with a hole in said lower portion thereof;
 c. a plurality of pedicular screws each having a self-tapping thread portion and a head portion, said self-tapping thread portion being of a size to extend through said hole in said bottom portion of said first rings and said head portion being of a size to be receivable within said first rings through said bore in said upper portion thereof;
 d. a rod, and means for assembling said rod to one of said first rings of each of said assemblies; and
 e. a plurality of cap means receivable within said bores of said first rings, whereby after said slideway is received through said slideway openings in a plurality of spaced first rings, pedicular screws are inserted with their self-tapping thread portions extending through said holes in said bottom portions of said first rings so that said head portions are seated within said slideway and said cap means are received in said bores to thereby secure said slideway relative to said first rings.

18. The spinal fixator of claim 17 in which said head portion of said pedicular screws is generally spherical and each of said cap means includes a lower surface having an arcuate profile which is complementary to said head portion of said pedicular screws.

19. The spinal fixator of claim 17 in which each of said assemblies includes a second ring having upper and lower portions and opposing side walls, each of said second rings defining a slideway opening of a profile to cooperatively receive said slideway therethrough, said second rings having a bore in said upper portion thereof which is aligned with a hole in said lower portion thereof, cap means receivable within said bore of said second ring, and said second ring including a plate extending outwardly from said lower portion thereof having a slot therein through which a pedicular screw is receivable.

* * * * *